United States Patent
Palladino et al.

(10) Patent No.: US 8,808,753 B2
(45) Date of Patent: *Aug. 19, 2014

(54) METHODS FOR TREATING PUSTULAR PSORIASIS

(71) Applicant: Stemnion, Inc., Pittsburgh, PA (US)

(72) Inventors: Linda O Palladino, Stormville, NY (US); Vivienne S Marshall, San Antonio, TX (US); Charlotte A Emig, Gibsonia, PA (US)

(73) Assignee: Stemnion, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/786,691

(22) Filed: Mar. 6, 2013

(65) Prior Publication Data

US 2013/0183387 A1 Jul. 18, 2013

Related U.S. Application Data

(62) Division of application No. 12/215,092, filed on Jun. 25, 2008.

(60) Provisional application No. 60/937,231, filed on Jun. 26, 2007.

(51) Int. Cl.
| | |
|---|---|
| *A61K 35/50* | (2006.01) |
| *A61K 8/98* | (2006.01) |
| *A61K 35/48* | (2006.01) |
| *A61K 31/56* | (2006.01) |
| *A61K 45/06* | (2006.01) |

(52) U.S. Cl.
CPC ............... *A61K 35/50* (2013.01); *A61K 8/982* (2013.01); *A61K 35/48* (2013.01); *A61K 31/56* (2013.01); *A61K 45/06* (2013.01); *A61K 5/0616* (2013.01)
USPC .......... 424/583; 424/93.7; 424/529; 424/577; 424/582

(58) Field of Classification Search
CPC . A61K 39/39541; A61K 39/00; A61K 35/50; C12N 9/1044
See application file for complete search history.

(56) References Cited

U.S. PATENT DOCUMENTS

| | | |
|---|---|---|
| 2006/0222634 A1 | 10/2006 | Clarke et al. |
| 2007/0231297 A1 | 10/2007 | Smith et al. |
| 2009/0004161 A1 * | 1/2009 | Palladino et al. ............ 424/93.7 |

FOREIGN PATENT DOCUMENTS

GB     2110531     6/1983

OTHER PUBLICATIONS

Kamiya, K., et al., 2005, Experimental Eye Research 80:671-679.

* cited by examiner

*Primary Examiner* — Blaine Lankford
(74) *Attorney, Agent, or Firm* — Linda O. Palladino; Gail M. Kempler

(57) ABSTRACT

The invention is directed to methods for treating pustular conditions of the skin, for example, acne. Such methods utilize novel compositions, including but not limited to extraembryonic cytokine secreting cells (herein referred to as ECS cells), including, but not limited to, amnion-derived multipotent progenitor cells (herein referred to as AMP cells), conditioned media derived therefrom (herein referred to as amnion-derived cellular cytokine solution or ACCS), cell lysates derived therefrom, and cell products derived therefrom, each alone or in combination.

7 Claims, No Drawings

METHODS FOR TREATING PUSTULAR PSORIASIS

CROSS-REFERENCE TO RELATED APPLICATIONS

This application is a divisional application of U.S. application Ser. No. 12/215,092, filed Jun. 25, 2008 and claims priority under 35 USC §119(e) of U.S. Provisional Application No. 60/937,231, filed Jun. 26, 2007, the entireties of which are incorporated herein by reference.

FIELD OF THE INVENTION

The field of the invention is directed to methods for treating pustular conditions of the skin. Such methods utilize novel compositions, including but not limited to extraembryonic cytokine secreting cells (herein referred to as ECS cells), including, but not limited to, amnion-derived multipotent progenitor cells (herein referred to as AMP cells), conditioned media derived therefrom (herein referred to as amnion-derived cellular cytokine solution or ACCS), cell lysates derived therefrom, and cell products derived therefrom, each alone or in combination.

BACKGROUND OF THE INVENTION

Generalized pustular conditions of the skin include pustular psoriasis, Reiter's disease and subcorneal pustular dermatosis. Medications can cause generalized pustular eruptions (i.e. exanthematous pustulosis) or more localized reactions (i.e. acneiform drug eruptions) which usually involve the face, chest and back. Localized pustular eruptions are seen on the hands and feet in adults with pustulosis palmaris et plantaris and acrodermatitis continua; on the face in patients with acne vulgaris, rosacea, and perioral dermatitis; and on the trunk and/or extremities in patients with folliculitis. A separate condition known as eosinophilic folliculitis occurs in individuals with advanced human immunodeficiency disease.

Acne vulgaris (acne) is a multifactorial inflammatory skin condition caused by changes in the pilosebaceous units, which are skin structures consisting of a large, multilobed sebaceous gland, a rudimentary hair and a wide follicular canal lined with stratified squamous epithelium. The pilosebaceous units are found over most of the body surface but are largest and most numerous on the face, chest and upper back. Acne is the most common pustular condition of the skin, disfiguring people with inflammatory and non-inflammatory lesions (including pustules, papules and comedones) during the active phase, and with atrophic scars afterwards. The condition is most common in puberty and in most instances diminishes over time, disappearing or at least decreasing after the person reaches the early twenties. However, some individuals continue to suffer from acne throughout adulthood.

The basic lesion of acne is the microcomedo which forms from an accumulation of sebum, the sebaceous gland secretion, and keratinous debris from skin cells and results in a visible closed comedo or whitehead. Its continued distension causes an open comedo, or blackhead, which gets its dark color from oxidized melanin. Blackheads and microcysts are noninflammatory lesions of acne, but some comedones evolve into inflammatory papules, pustules, or nodules, and can become chronic granulomatous lesions. When inflammation develops, neutrophil infiltration occurs. These neutrophils secrete hydrolytic enzymes that cause further damage. In pustules, neutrophils are present much earlier. More persistent lesions exhibit granulomatous histology that can lead to scarring.

The main goals when treating acne are to minimize the number and severity of lesions, prevent scarring, limit disease duration, and reduce the social and psychological stress that affects many patients, particularly teenagers. Conventional treatment is directed at correcting the three major factors that seem to cause acne: (1) androgenic stimulation of the sebaceous glands and increased sebum production; (2) abnormal keratinization and impaction in the pilosebaceous canal causing obstruction of sebum flow; and (3) proliferation of *P. acnes*, the bacteria that infects acne lesions. Thus, topical agents that remove comedones (i.e. topical retinoids) are particularly effective because they normalize desquamation within the follicular orifice, which allows the sebum to flow freely onto the surface of the skin. Retinoids such as dalpalene, tretinoin, and tazarotene have been shown to have efficacy in treating mild to moderate acne, but all three are reported to have skin-irritating side effects including erythema, pruritis, burning/stinging and scaling/flaking (Physicians' Desk Reference®, 56th ed. 2002, p. 2523, hereinafter referred to as "PDR"). In fact, the side effects of retinoid use are so extreme that many individuals cannot tolerate topical application of these agents at all.

There are many products on the market to treat acne. Unfortunately, many of them have no scientifically proven effects. Those few products which are useful typically show little improvement in the first week or two of use, after which the acne decreases over approximately 3 months, then improvement levels off. Short courses of cortisone, antibiotics and many laser therapies offer a quick reduction in the redness, swelling and inflammation when used correctly, but none of these empty the pore of all the materials that trigger the inflammation.

Treatment regimens often involve exfoliation to reduce or prevent shedding of dead skin cells into the pore and causing its blockage. This can be done either mechanically using an abrasive cloth or a liquid scrub, or chemically. Common chemical exfoliating agents include salicylic acid and glycolic acid, which encourage the destruction of the top layer of skin cells to prevent a build-up of dead cells which combine with sebum to block pores. Chemical exfoliation also helps to unblock already clogged pores. Depending on the type of exfoliation used, some visible flaking of the skin is possible. Moisturizers and anti-acne topical treatments containing chemical exfoliating agents are available over-the-counter. However, mechanical exfoliation is less commonly used as many benefits derived from the exfoliation are negated by the act of mechanically rubbing and irritating the skin.

In addition, over-the-counter topical bactericidal products containing benzoyl peroxide are common used. Benzoyl peroxide kills *P. acnes*, which may help prevent formation of new lesions, and acts as a keratolytic (a chemical that dissolves the keratin plugging the pores). Unlike antibiotics, benzoyl peroxide has the advantage of being a strong oxidizer and thus does not appear to generate bacterial resistance. However, it routinely causes dryness, local irritation and redness so it should be combined with suitable moisturizers. Antibiotics such as tetracycline are also useful, as are anti-inflammatory agents such as topical steroids.

Phototherapy using intense blue light generated by fluorescent lighting, dichroic bulbs, LEDs or lasers are also useful treatments. Used twice weekly, phototherapy has been shown to reduce the number of acne lesions significantly and is even more effective when applied daily. The mechanism appears to be that a porphyrin (Coproporphyrin III) produced within *P.*

*acnes* generates free radicals when irradiated by blue light. These free radicals ultimately kill the bacteria. Since porphyrins are not otherwise present in skin, and no UV light is employed, it appears to be safe and has been approved by the FDA. Unlike most of the other treatments, few if any negative side effects are typically experienced, and the development of bacterial resistance to the treatment seems very unlikely.

Other less common treatments include Azelaic acid (brand names Azelex, Finevin, Skinoren); orally administered zinc gluconate; sulfur as a topical treatment in soaps, creams, shampoos, etc., due to its antibacterial and antifungal properties; Tea Tree Oil (Melaleuca Oil), which has been shown to be an effective anti-inflammatory in skin infections; heat therapy at a specific temperature to kill the *P. acnes* bacteria; nicotinamide (Vitamin $B_3$) used topically in the form of a gel, which seems to have anti-inflammatory properties; and laser surgery, which has been in use for some time to reduce the scars left behind by acne, for prevention of acne formation itself.

In summary, currently available treatments have exhibited limited success, most have side effects and some are costly. There is no cure for acne on the market today. Therefore, it is an object of the instant invention to provide treatments and a cure for this unmet medical need as well as treatments for other pustular conditions of the skin.

BRIEF SUMMARY OF THE INVENTION

The compositions described herein have previously been shown to be useful in treating wounds (details are contained in U.S. Publication No. 2006-0222634-A1 and U.S. Publication No. 2007-0231297 A1, which are incorporated herein by reference). In particular, the compositions described herein have been demonstrated to accelerate wound healing in chronic, infected wounds, even though the compositions themselves are not able to reduce bioburden in such infected wounds. Therefore, the compositions described herein may accelerate healing of pustular conditions of the skin faster and with less scarring than other available treatments, and such accelerated healing may be further enhanced when used in combination with antibiotic treatment or other treatment modalities that are able to reduce bioburden that may be present in pustular conditions of the skin. It is an object of the instant invention to provide novel methods for treating pustular conditions of the skin and such methods utilize novel compositions, including but not limited to extraembryonic cytokine secreting cells (herein referred to as ECS cells), including, but not limited to, amnion-derived multipotent progenitor cells (herein referred to as AMP cells), conditioned media derived therefrom (herein referred to as amnion-derived cellular cytokine solution or ACCS), cell lysates derived therefrom, and cell products derived therefrom, each alone and/or in combination with each other and/or with other agents including active and/or inactive agents.

Accordingly, first aspect of the invention is a method for treating a pustular condition of the skin in a patient in need thereof comprising administering to the patient a therapeutically effective amount of one or more compositions comprising ECS cells, conditioned media derived therefrom, cell lysate derived therefrom or cell products derived therefrom. In one embodiment the treatment causes a reduction in inflammation of the pustular condition. In another embodiment the treatment causes accelerated healing of the pustular condition. In still another embodiment the treatment causes reduced scarring of the skin following healing of the pustular condition. In a particular embodiment the pustular condition of the skin is acne.

In other preferred embodiments the ECS cells are AMP cells. In particular embodiments the AMP cells are pooled AMP cells. In yet another particular embodiment the conditioned media is ACCS. And in still another particular embodiment the ACCS is pooled ACCS.

A second aspect of the invention is one in which the ECS cells are partially differentiated or fully differentiated. In one embodiment the ECS cells are AMP cells and the AMP cells are partially differentiated or fully differentiated. In other embodiments a mixture of undifferentiated, partially differentiated or fully differentiated cells are used in practicing the methods of the invention.

A third aspect of the invention is one in which the ECS cells, including AMP cells, conditioned media derived therefrom, cell lysate derived therefrom or cell products derived therefrom are administered in combination with other agents or therapies. In one embodiment of this aspect of the invention the other agents are active agents. In particular embodiments the active agents are steroids, topical bactericidal agents, or antibiotics. In other particular embodiments the other therapy is mechanical exfoliation, chemical exfoliation, phototherapy or laser therapy.

Other features and advantages of the invention will be apparent from the accompanying description, examples and the claims. The contents of all references, pending patent applications and published patents, cited throughout this application are hereby expressly incorporated by reference. In case of conflict, the present specification, including definitions, will control.

DEFINITIONS

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristic of secreting a unique combination of physiologically relevant cytokines in a physiologically relevant temporal manner into the extracellular space or into surrounding culture media. In one embodiment, the ECS cells secrete at least one cytokine selected from VEGF, Angiogenin, PDGF and TGFβ2 and at least one MMP inhibitor selected from TIMP-1 and TIMP-2. In another embodiment, the ECS cells secrete more than one cytokine selected from VEGF, Angiogenin, PDGF and TGFβ2 and more than one MMP inhibitor selected from TIMP-1 and TIMP-2. In a preferred embodiment, the ECS cells secrete the cytokines VEGF, Angiogenin, PDGF and TGFβ2 and the MMP inhibitors TIMP-1 and TIMP-2. The physiological range of the cytokine or cytokines in the unique combination is as follows: ~5-16 ng/mL for VEGF, ~3.5-4.5 ng/mL for Angiogenin, ~100-165 μg/mL for PDGF, ~2.5-2.7 ng/mL for TGFβ2, ~0.68 μg mL for TIMP-1 and ~1.04 μg/mL for TIMP-2. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety.

As used herein, the term "amnion-derived multipotent progenitor cell" or "AMP cell" means a specific population of ECS cells that are epithelial cells derived from the amnion. In addition to the characteristics described above for ECS cells, AMP cells have the following characteristics. They have not been cultured in the presence of any animal—derived products, making them and cell products derived from them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated AMP cells will not react with antibodies to the stem/progenitor cell markers c-kit (CD117) and Thy-1 (CD90). Several procedures used to obtain cells from full term or pre-term placenta are known in the art (see, for example, U.S. 2004/0110287; Anker et al., 2005, Stem Cells 22:1338-1345; Ramkumar et al., 1995, Am. J. Ob. Gyn. 172:493-500). However, the methods used herein provide improved compositions and populations of cells. AMP cells have previously been described as "amnion-derived cells" (see U.S. Provisional Application Nos. 60/666,949, 60/699,257, 60/742,067, U.S. Provisional Application No. 60/813,759, U.S. application Ser. No. 11/333,849, U.S. application Ser. No. 11/392,892, and PCTUS06/011392, each of which is incorporated herein in its entirety).

By the term "animal-free" when referring to certain compositions, growth conditions, culture media, etc. described herein, is meant that no animal-derived materials, such as animal-derived serum, other than human materials, such as native or recombinantly produced human proteins, are used in the preparation, growth, culturing, expansion, or formulation of the certain composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, the term "differentiation" means the process by which cells become progressively more specialized.

As used herein, the term "differentiation efficiency" means the percentage of cells in a population that are differentiating or are able to differentiate.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from ECS cells, including AMP cells.

As used herein, the term "amnion-derived cellular cytokine solution" or "ACCS" means conditioned medium that has been derived from AMP cells or expanded AMP cells. Amnion-derived cellular cytokine solution has previously been referred to as "amnion-derived cellular cytokine suspension".

The term "physiological level" as used herein means the level that a substance in a living system is found and that is relevant to the proper functioning of a biochemical and/or biological process.

As used herein, the term "pooled" means a plurality of compositions that have been combined to create a new composition having more constant or consistent characteristics as compared to the non-pooled compositions. For example, pooled ACCS cells have more constant or consistent characteristics compared to non-pooled ACCS cells.

The term "therapeutically effective amount" means that amount of a therapeutic agent necessary to achieve a desired physiological effect (i.e. promote healing of acne).

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

As used herein, the term "pharmaceutically acceptable" means that the components, in addition to the therapeutic agent, comprising the formulation, are suitable for administration to the patient being treated in accordance with the present invention.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

The term "transplantation" as used herein refers to the administration of a composition comprising cells that are either in an undifferentiated, partially differentiated, or fully differentiated form into a human or other animal.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

The term "topical administration" and "administered topically" are art-recognized terms and refer to modes of administration other than parenteral and enteral administration, usually by application to the skin.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scarring and/or the wounded area possesses tissue strength that is closer to that of uninjured tissue and/or the wounded tissue attains some degree of functional recovery.

As used herein, the term "pustular conditions of the skin" means any skin disorder in which skin eruptions occur. Such eruptions may or may not be infected.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Uses

Acne vulgaris (acne) is an inflammatory skin disease caused by changes in the pilosebaceous units, which are skin structures consisting of a hair follicle and its associated sebaceous gland and duct. Treatment typically involves one or more of exfoliation to reduce or prevent shedding of dead skin cells into the pore and causing its blockage, treating with antibiotics and/or topical bactericidal agents to kill *P. acnes*, applying topical steroid treatment to reduce inflammation, phototherapy and laser therapy. In accordance with the subject invention, Applicants have found that topical application of ECS cells and/or conditioned medium derived therefrom, and in particular, AMP cells and/or ACCS, including pooled AMP cells and/or pooled ACCS, accelerates wound healing and reduces or eliminates scarring (see U.S. Publication No. 2006-0222634 and U.S. Publication No. 2007-0231297, each of which is incorporated herein in its entirety) and that such topical application is suitable for treating, accelerating healing, reducing occurrence and reducing or eliminating the formation of scars following healing of pustular skin lesions, i.e. acne.

Pustular psoriasis is an uncommon form of psoriasis. People with pustular psoriasis have clearly defined, raised bumps on the skin that are filled with pus (pustules). The skin under and around these bumps is red. Large portions of the skin may redden. The compositions and methods of the invention are useful in treating pustular psoriasis.

Subcorneal pustular dermatosis is a chronic vesiculopustular eruption of unknown etiology. The pustules are usually localized to the groin, axillae, submammary areas, and the flexor areas of the limbs. They resolve within a few days resulting in superficial scale-crust formation. The compositions and methods of the invention are useful in treating subcorneal pustular dermatosis.

Generalized pustular eruptions (i.e. exanthematous pustulosis) or more localized reactions (i.e. acneiform drug eruptions) usually involve the face, chest and back. The compositions and methods of the invention are useful in treating such pustular eruptions.

Acrodermatitis continua is a variant of pustular psoriasis, with chronic inflammation of limbs that in some cases becomes generalized. The compositions and methods of the invention are useful in treating acrodermatitis continua.

Rosacea is an inflammatory skin disease that causes facial redness. Some of its characteristics include small, red, pus-filled bumps or pustules. Rosacea affects mostly adults, usually people with fair skin, between the ages of 30 and 60. About 14 million Americans have this chronic skin condition. Although it's more common in women, men may develop more apparent signs of the disorder. Left untreated, rosacea tends to be progressive. The compositions and methods of the invention are useful in treating rosacea.

Perioral dermatitis is a facial rash that tends to occur around the mouth. Most often it is red and slightly scaly or bumpy. Any itching or burning is mild. It may spread up around the nose, and occasionally the eyes while avoiding the skin adjacent to the lips. Perioral dermatitis may come and go for months or years. The compositions and methods of the invention are useful in treating perioral dermatitis.

Folliculitis is inflammation of one or more hair follicles. The condition may occur anywhere on the skin. Common symptoms include a rash, itching, and pimples or pustules near a hair follicle in the neck, groin, or genital area. The compositions and methods of the invention are useful in treating folliculitis.

Eosinophilic folliculitis. There are several variants of eosinophilic folliculitis, which is also known as 'eosinophilic pustular folliculitis' or 'Ofuji disease'. All variants present with itchy papules (bumps) or pustules. Eosinophilic folliculitis is rare and more often affects males than females. Variants include: Classic type—this occurs most commonly in Japan; Eosinophilic folliculitis associated with advanced Human Immunodeficiency Virus (HIV) infection; Infantile type; Cancer-associated variant; Medication-associated variant. The compositions and methods of the invention are useful in treating eosinophilic folliculitis Obtaining and Culturing of Cells ECS—Various methods for isolating cells from the extraembryonic tissue, which may then be used to produce the ECS cells of the instant invention are described in the art (see, for example, US2003/0235563, US2004/0161419, US2005/0124003, U.S. Provisional Application Nos. 60/666, 949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179).

Identifying ECS cells—Once extraembryonic tissue is isolated, it is necessary to identify which cells in the tissue have the characteristics associated with ECS cells (see definition above). For example, cells are assayed for their ability to secrete a unique combination of cytokines into the extracellular space or into surrounding culture media. Suitable cells are those in which the cytokine or cytokines occurs in the physiological range of ~5.0-16 ng/mL for VEGF, ~3.5-4.5 ng/mL for Angiogenin, ~100-165 µg/mL for PDGF, ~2.5-2.7 ng/mL for TGFβ2, ~0.68 µg mL for TIMP-1 and ~1.04 µg/mL for TIMP-2.

AMP cells—In a particular embodiment, AMP cell compositions are prepared using the steps of a) recovery of the amnion from the placenta, b) dissociation of the amnion epithelial cells from the amniotic membrane, c) isolating AMP cells from the amnion epithelial cells, d) culturing of the AMP cells in a basal medium with the addition of a naturally derived or recombinantly produced human protein; and optionally d) further proliferation of the cells using additional additives and/or growth factors. Details are contained in U.S. Publication No. 2006-0222634-A1, which is incorporated herein by reference.

AMP cells are cultured as follows: The AMP cells are cultured in a basal medium. Such medium includes, but is not limited to, Epilife (Cascade Biologicals), Opti-pro, VP-SFM, IMDM, Advanced DMEM, K/O DMEM, 293 SFM II (all made by Gibco; Invitrogen), HPGM, Pro 293S-CDM, Pro 293A-CDM, UltraMDCK, UltraCulture (all made by Cambrex), Stemline I and Stemline II (both made by Sigma-Aldrich), DMEM, DMEM/F-12, Ham's F12, M199, and other comparable basal media. Such media should either contain human protein or be supplemented with human protein. As used herein a "human protein" is one that is produced naturally or one that is produced using recombinant technology. "Human protein" also is meant to include a human fluid or derivative or preparation thereof, such as human serum or amniotic fluid, which contains human protein. Details on this procedure are contained in U.S. Publication No. 2006-0222634-A1, which is incorporated herein by reference.

In a most preferred embodiment, the cells are cultured using a system that is free of animal products to avoid xeno-contamination. In this embodiment, the culture medium is Stemline I or II, Opti-pro, or DMEM, with human albumin added up to concentrations of 10%. The invention further contemplates the use of any of the above basal media wherein animal-derived proteins are replaced with recombinant human proteins and animal-derived serum, such as BSA, is replaced with human albumin. In preferred embodiments, the media is serum-free in addition to being animal-free. Details on this procedure are contained in U.S. Publication No. 2006-0222634-A1, which is incorporated herein by reference.

In alternative embodiments, where the use of non-human serum is not precluded, such as for in vitro uses, the culture medium may be supplemented with serum derived from mammals other than humans, in ranges of up to 40%.

Additional proliferation—Optionally, other proliferation factors are used. In one embodiment, epidermal growth factor (EGF), at a concentration of between 0-1 µg/mL is used. In a preferred embodiment, the EGF concentration is around 10 ng/mL. Alternative growth factors which may be used include, but are not limited to, TGFα or TGFβ (5 ng/mL; range 0.1-100 ng/mL), activin A, cholera toxin (preferably at a level of about 0.1 µg/mL; range 0-10 µg/mL), transferrin (5 µg/mL; range 0.1-100 µg/mL), fibroblast growth factors (bFGF 40 ng/mL (range 0-200 ng/mL), aFGF, FGF-4, FGF-8; (all in range 0-200 ng/mL), bone morphogenic proteins (i.e. BMP-4) or other growth factors known to enhance cell proliferation.

Generation of Conditioned Medium

ECS conditioned medium—is obtained as described below for ACCS, except that ECS cells are used.

Generation of ACCS—The AMP cells of the invention can be used to generate ACCS. In one embodiment, the AMP cells are isolated as described herein and $1 \times 10^6$ cells/mL are seeded into T75 flasks containing between 5-30 mL culture medium, preferably between 10-25 mL culture medium, and most preferably about 10 mL culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. It is also contemplated by the invention that ACCS be formulated for sustained-release following collection. Skilled artisans are familiar with cryopreservation lyophilization, and sustained-release formulation methodologies.

The ACCS of the invention is characterized by assaying for physiologically relevant cytokines secreted in the physiologically relevant range of ~5-16 ng/mL for VEGF, ~3.5-4.5 ng/mL for Angiogenin, ~100-165 µg/mL for PDGF, ~2.5-2.7 ng/mL for TGFβ2, ~0.68 µg mL for TIMP-1 and ~1.04 µg/mL for TIMP-2. ACCS has also been shown to contain Thymosin β4, a factor known to enhance wound healing.

The compositions of the invention can be prepared in a variety of ways depending on the intended use of the compositions. For example, a composition useful in practicing the invention may be a liquid comprising an agent of the invention, i.e. ECS cells, including AMP cells and/or ACCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like, suitable for topical administration.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions

The present invention provides pharmaceutical compositions of ECS cells, including AMP cells and/or ACCS and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits

The invention also provides for an article of manufacture comprising packaging material and a pharmaceutical composition of the invention contained within the packaging material, wherein the pharmaceutical composition comprises compositions of ECS cells, including AMP cells and/or ACCS. The packaging material comprises a label or package insert which indicates that the ECS cells, including AMP cells and/or ACCS can be used for treating skin lesions, for example, acne.

Formulation, Dosage and Administration

Compositions comprising ECS cells, including AMP cells and/or ACCS may be administered to a subject to provide various cellular or tissue functions, for example, to treat skin lesions, for example, acne. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use in treating skin lesions, for example, acne. The compositions may also be administered to the recipient in one or more physiologically acceptable carriers. Carriers for the cells may include but are not limited to solutions of phosphate buffered saline (PBS) or lactated Ringer's solution containing a mixture of salts in physiologic concentrations.

One of skill in the art may readily determine the appropriate concentration, or dose, of the ECS cells, including AMP cells and/or ACCS, for a particular purpose. The skilled artisan will recognize that a preferred dose is one which produces a therapeutic effect, such as treating skin disorders, for example, acne, in a patient in need thereof. One preferred dose is in the range of about 0.1-to-1000 µL per square centimeter of applied area. Other preferred dose ranges are 1.0-100 µL per square centimeter of applied area and about 0.01-to-50.0 µL per square centimeter of applied area. Of course, proper doses of the ECS cells, including AMP cells and/or ACCS will require empirical determination at time of use based on several variables including but not limited to the severity of disease, disorder or condition being treated; patient age, weight, sex, health; other medications and treatments being administered to the patient; and the like. One of skill in the art will also recognize that number of doses (dosing regimen) to be administered needs also to be empirically determined based on, for example, severity of disease, disorder or condition being treated. In a one embodiment, one dose is sufficient. Other embodiments contemplate, 2, 3, 4, or more doses. In still other embodiments, treatment may involve multiple doses over weeks, months or longer.

The present invention provides a method of treating skin disorders, for example, acne, by administering to a subject ECS cells, including AMP cells and/or ACCS in a therapeutically effective amount. By "therapeutically effective amount" is meant the dose of ECS cells, including AMP cells and/or ACCS that is sufficient to elicit a therapeutic effect. Thus, the concentration of ECS cells, including AMP cells and/or ACCS in an administered dose unit in accordance with the present invention is effective in the treatment skin lesions, i.e. acne.

In further embodiments of the present invention, at least one additional agent may be combined with the ECS cells, including AMP cells and/or ACCS. Such agents include, for example, steroids or topical bactericidal agents. In addition to these agents, it may be desirable to co-administer other agents, including active agents and/or inactive agents, with the ECS cells, including AMP cells and/or ACCS. Active agents include but are not limited to growth factors, cytokines, chemokines, antibodies, antibiotics, anti-fungals, anti-virals, other cell types, and the like. Inactive agents include carriers, diluents, stabilizers, gelling agents, delivery vehicles, ECMs (natural and synthetic), scaffolds, and the like. When the ECS cells, including AMP cells and/or ACCS are administered conjointly with other pharmaceutically active agents even less of the ECS cells, including AMP cells and/or ACCS may be needed to be therapeutically effective.

ECS cells, including AMP cells and/or ACCS can be administered topically to a target site of a subject, or may be administered by other means. Specific, non-limiting examples of administering AMP cells and/or ACCS to subjects may also include administration by subcutaneous injection, intramuscular injection or intradermal injection.

The timing of administration of ECS cells, including AMP cells and/or ACCS will depend upon the severity of the skin condition being treated. In a preferred embodiment, the ECS cells, including AMP cells and/or ACCS, are administered as soon as possible after diagnosis. In other preferred embodiments, the ECS cells, including AMP cells and/or ACCS are administered more than one time following diagnosis.

Also contemplated by the methods of the invention are compositions comprising partially or fully differentiated ECS cells, including AMP cells, or combinations thereof. Such partially or fully differentiated cell compositions are obtained by treating ECS cells, including AMP cells, with appropriate reagents and under appropriate conditions wherein the cells undergo partial or complete differentiation. Skilled artisans are familiar with conditions capable of effecting such partial or complete differentiation. The cells may be treated under differentiating conditions prior to use (i.e. transplantation, administration, etc.), simultaneously with use or post-use. In certain embodiments, the cells are treated under differentiation conditions before and during use, during and after use, before and after use, or before, during and after use.

Skilled artisans will recognize that any and all of the standard methods and modalities for treating skin disorders, for example, acne, currently in clinical practice and clinical development are suitable for practicing the methods of the invention. Routes of administration, formulation, co-administration with other agents (if appropriate) and the like are discussed in detail elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of AMP Cell Compositions

Recovery of AMP cells—AMP cells were dissociated from starting amniotic membrane using the dissociation agents PXXIII, and trypsin. The average weight range of an amnion was 18-27 g. The number of cells recovered per g of amnion was about 10-15×10⁶ for dissociation with PXXIII and 5-8×10⁶ for dissociation with trypsin.

Method of obtaining selected AMP cells: Cells were plated immediately upon isolation from the amnion. After ~2 days in culture non-adherent cells were removed and the adherent cells were kept. This attachment to a plastic tissue culture vessel is the selection method used to obtain the desired population of cells. Adherent and non-adherent AMP cells appear to have a similar cell surface marker expression profile but the adherent cells have greater viability and are the desired population of cells. Adherent AMP cells were cultured until they reached ~120,000-150,000 cells/cm². At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reach ~120,000-150,000 cells/cm², they were collected and cryopreserved. This collection time point is called p0.

Example 2

Generation of ACCS

The AMP cells of the invention can be used to generate ACCS. The AMP cells were isolated as described herein and 1×10⁶ cells/mL were seeded into T75 flasks containing ~10 mL culture medium. The cells were cultured until confluent, the medium was changed and ACCS was collected 3 days post-confluence. Skilled artisans will recognize that other embodiments for collecting ACCS from confluent cultures, such as using other tissue culture vessels, including but not limited to cell factories, flasks, hollow fibers, or suspension culture apparatus, are also contemplated by the methods of the invention. It is also contemplated by the instant invention that the ACCS be cryopreserved, lyophilized or formulated, for example, into sustained-release formulations following collection.

Example 3

Generation of Pooled ACCS

ACCS was obtained essentially as described above. In certain embodiments, ACCS was collected multiple times from an AMP culture derived from one placenta and these multiple ACCS collections were pooled together. Such pools are referred to as "SP pools" (more than one ACCS collection/one placenta). In another embodiment, AMP cultures were derived from several placentas, i.e. from 5 or 10 placentas. The AMP cells from each placenta were cultured and one ACCS collection from each culture was collected and then they were all pooled. These pools are termed "MP1 pools" (one ACCS collection/placenta, multiple placentas). In yet another embodiment, AMP cell cultures were derived from several placentas, i.e. from 5 or 10 placentas. The AMP cells from each placenta were cultured and more than one ACCS collection was performed from each AMP cell culture and then pooled. These pools are termed "MP2 pools" (more than one ACCS collection/placenta, multiple placentas).

Example 4

Detection of Growth Factors and Cytokines Important in Treating Pustular Conditions of the Skin To determine which growth factors and/or cytokines important in treating acne may be secreted by the AMP cells of the present invention, ACCS was isolated from cell cultures that were seeded onto tissue culture treated flasks at a density of ~40,000 cells per cm². Cells were cultured in a proprietary serum-free medium supplemented with 10 ng/mL of EGF. Culture media was exchanged every 2 days during the growth period. After cells reached near confluency (~1-2 wk after isolation), fresh media was applied and ACCS was collected after three days and stored at −80° C. for subsequent analysis.

ACCS was analyzed for secreted factor content via antibody arrays, ELISA, multiplex and mass spectroscopy assays.

Results—The following relevant factors were detected in ACCS by antibody arrays, ELISA, and/or multiplex assays: VEGF, PDGF, Angiogenin, TGFβ2, TIMP-1 and TIMP-2. Thymosin β4 was detected by mass spectroscopy.

Example 5

Effects of ACCS in an Animal Model of Acute Wound Healing

An art-accepted animal model of acute excisional granulating wound was used to evaluate the effect of ACCS on wound healing. Details are contained in U.S. Publication No. 2006-0222634-A1 and U.S. Publication No. 2007-0231297 A1, which are incorporated herein by reference. The animals were divided into the following groups: Group I—ACCS, non-infected; Group II—Unconditioned media; Group III—ACCS, infected; Group IV—Unconditioned media, infected.

Analog tracings were made every 72 hours onto acetate sheets of both open wound areas and of the advancing full-thickness skin edges of all wounds. To eliminate site-related variability in the wounds, only the three caudal wounds were measured for statistical purposes, since the most cephalad wound has been shown to demonstrate different healing characteristics. Wound area calculations were performed with the use of digital planimetry (Sigma Scan; Jandel Scientific, Corte Modera, Calif.). Weekly quantitative bacterial analyses were performed on a subset of wounds in each group and are expressed as CFUs/g of tissue.

After all four wounds of each animal were completely epithelialized as determined by visual inspection, the animals were euthanized and the entire dorsum of the rat including the panniculus carnosus was removed. A 1cm wide skin strip perpendicular to each resultant scar, was harvested for breaking strength analysis. An Instron tensiometer (Model No. 4201; Instron Corp., Canton, Mass.) with a 5 kg tension load cell and cross head speed of 10 mm/min was used. Breaking strength is defined as the force required to rupture the scar and is reported in kilograms.

Results—The application of ACCS overcomes the inhibition of wound healing caused by bacteria and shifts the healing trajectory in contaminated wounds to that of near normal healing.

Example 6

Effects of ACCS in an Animal Model of Chronic Wound Healing

An art-accepted animal model for chronic granulating wound was used to study the effects of ACCS on chronic wound healing (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990).

Results: ACCS was effective in not allowing proliferation of tissue bacterial bioburden. ACCS allowed accelerated healing of the granulating wound significantly faster than the non-treated infected control groups.

Example 7

Therapeutic Potential of ECS Cells and/or Conditioned Media, including AMP Cells and ACCS, in Animal Models of Acne Several art-accepted animal models of acne are described in "Acne, William James Cuniff, Published 1989 Taylor & Francis, Chapter 14, page 246-249." The compositions of the invention are tested in these animal models to assess their therapeutic potential.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for treating pustular psoriasis in a patient in need thereof comprising administering to the patient a therapeutically effective amount of of Amnion-derived Multipotent Progenitor (AMP) cell lysate.

2. The method of claim 1 wherein such treatment causes accelerated healing of the pustular psoriasis.

3. The method of claim 1 wherein such treatment causes reduced scarring of the skin following healing of the pustular psoriasis.

4. The method of claim 1 wherein the AMP cell lysate is administered in combination with other agents or therapies.

5. The method of claim 4 wherein the other agents are active agents.

6. The method of claim 5 wherein the active agents are selected from the group consisting of steroids and antibiotics.

7. The method of claim 4 wherein the other therapy is selected from the group consisting of phototherapy and laser therapy.

* * * * *

UNITED STATES PATENT AND TRADEMARK OFFICE
CERTIFICATE OF CORRECTION

PATENT NO. : 8,808,753 B2
APPLICATION NO. : 13/786691
DATED : August 19, 2014
INVENTOR(S) : Linda O. Palladino, Vivienne S. Marshall and Charlotte A. Emig It is certified that error appears in the above-identified patent and that said Letters Patent is hereby corrected as shown below:

In the Claims

Column 18, Claim 1, Line 7: Delete the extra "of".

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*